US006596781B1

(12) United States Patent
Schinski

(10) Patent No.: US 6,596,781 B1
(45) Date of Patent: Jul. 22, 2003

(54) INTEGRATED PROCESS FOR PREPARING FISCHER-TROPSCH PRODUCTS AND ACETIC ACID FROM SYNTHESIS GAS

(75) Inventor: William L. Schinski, San Rafael, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 10/137,698

(22) Filed: May 2, 2002

(51) Int. Cl.[7] .................. C07C 27/00; C07C 51/12; C07C 51/14; C07C 67/36; C10G 35/06
(52) U.S. Cl. ............... 518/700; 518/702; 518/703; 518/715; 208/136; 562/519; 562/522; 562/890; 560/232
(58) Field of Search ............... 518/700, 702, 518/703, 715; 208/136; 562/519, 890, 522; 560/232

(56) References Cited

U.S. PATENT DOCUMENTS

| | | |
|---|---|---|
| 4,888,130 A | 12/1989 | Banquy |
| 4,971,683 A | 11/1990 | Meyer et al. |
| 5,189,203 A | 2/1993 | Hansen et al. |
| 5,218,140 A | 6/1993 | Wegman |
| 5,286,900 A | 2/1994 | Hansen et al. |
| 5,330,955 A | 7/1994 | Wegman |
| 5,659,077 A | 8/1997 | McFarlan |
| 5,728,871 A | 3/1998 | Joensen et al. |
| 5,840,969 A | 11/1998 | Joensen |
| 5,900,505 A | 5/1999 | Tustin et al. |
| 5,922,911 A | 7/1999 | Jones et al. |
| 6,127,432 A | 10/2000 | Wegman et al. |
| 6,175,039 B1 | 1/2001 | Voss |
| 6,232,352 B1 | 5/2001 | Vidalin |
| 6,254,807 B1 | 7/2001 | Schmidt et al. |

FOREIGN PATENT DOCUMENTS

| | | |
|---|---|---|
| EP | 0 526 974 B1 | 11/1995 |
| EP | 0 609 079 B1 | 7/1998 |

OTHER PUBLICATIONS $C_1$ to acetyls: catalysis and process, M.J. Howard, M.D. Jones, M.S. Roberts and S.A. Taylor, BP Chemicals Ltd., Hull Research and Technology Centre, Saitend, Hull HU12 8DS (UK), Catalysis Today, 18 (1993) 325–354 Elsevier Science Publishers B.V., Amsterdam.

Activity and Stability of Two Polymer–Supported Rhodium–Based Catalysts for the Vapour Phase Carbonylation of Methanol, N. De Blasio, E. Tempesti, A. Kaddouri, C. Mazzocchia, and D.J. Cole–Hamilton, Journal of Catalysis 176, 253–259 (1998), Article No. CA982030.

A study of Rh–Sm–V/SiO2 catalysts for the preparation of C2–oxygenates from syngas, H.Y. Luo, W. Zhang, H.W. Zhou, S.Y. Huang, P.Z. Lin, Y.J. Ding, L.W. Lin, Applied Catalysis A: General 214 (2001) 161–166.

Primary Examiner—J. Parsa
(74) Attorney, Agent, or Firm—James W. Ambrosius

(57) ABSTRACT

An integrated process for carrying out the production of Fischer-Tropsch products and acetic acid made using the methanol and carbonylation route which utilizes the hydrogen recovered from the methanol production to upgrade the Fischer-Tropsch products.

34 Claims, 1 Drawing Sheet

INTEGRATED PROCESS FOR PREPARING FISCHER-TROPSCH PRODUCTS AND ACETIC ACID FROM SYNTHESIS GAS

FIELD OF THE INVENTION

The present invention is directed to an integrated process for manufacturing Fischer-Tropsch products and acetic acid, methyl acetate, or acetic anhydride from synthesis gas preferably derived from reforming methane or natural gas.

BACKGROUND OF THE INVENTION

Processed natural gas, consisting essentially of methane (typically 85–95 volume percent) but with significant amounts of carbon dioxide present in some areas, may be directly used as a clean burning gaseous fuel for industrial heat and power plants, for the production of electricity, and to fire the kilns in the cement and steel industries. It is also useful as a chemical feedstock, but large-scale use for this purpose is largely limited to conversion to synthesis gas which in turn is used for the manufacture of methanol and ammonia. It is notable that for the foregoing uses, no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote regions where it may not be economical to transport the gas to market. For many of these remote fields, pipelining to bring the gas to potential users is not economically feasible. In such circumstances, it is desirable to convert the methane in the natural gas at the production site into more valuable and more easily transported products. Currently, one of the most important products made from methane is acetic acid. Products prepared from methane using the Fischer-Tropsch process also are becoming increasingly more important. Both acetic acid and Fischer-Tropsch products are prepared by first reforming methane into synthesis gas or syngas which is primarily a mixture of carbon monoxide and hydrogen. Synthesis gas may contain varying amounts of carbon dioxide, water, and unconverted light hydrocarbon feedstock. Impurities originally present in the natural gas, such as sulfur and nitrogen, may also be present. The methane may be reformed using oxygen according to the general formula:

$$2CH_4 + O_2 \rightarrow 2CO + 4H_2 \quad (1)$$

In addition, the methane may be reformed to synthesis gas using steam $$CH_4 + H_2O \rightarrow CO + 3H_2 \quad (2)$$

or by using carbon dioxide.

$$CH_4 + CO_2 \rightarrow 2CO + 2H_2 \quad (3)$$

While methane is the most important source of synthesis gas, other sources of synthesis gas have been described, as, for example, by the gasification of coal or the decomposition of methanol.

In the manufacture of acetic acid, the synthesis gas is first converted to methanol by an equilibrium reaction over a catalyst usually containing copper. This process step may be shown as:

$$CO + 2H_2 \leftrightarrows CH_3OH \quad (4)$$

Typically there will be about a 20% to 50% synthesis gas conversion per pass to methanol in this step. Carbon dioxide which is often present in significant amounts in the synthesis gas will also react with hydrogen to form methanol as shown in the following:

$$CO_2 + 3H_2 \rightarrow CH_3OH + H_2O \quad (5)$$

The methanol in turn is reacted with unreacted carbon monoxide in the presence of a suitable catalyst to make acetic acid in what is referred to in this disclosure as a carbonylation reaction. As noted above, reaction (4) is an equilibrium reaction, and the reverse reaction, i.e. the decomposition of methanol, may be used to generate a source of synthesis gas. The carbonylation reaction may be represented as follows:

$$CO + CH_3OH \rightarrow CH_3COOH \quad (6)$$

Unreacted hydrogen which passes along with the methanol and CO in the feed to the carbonylation reaction has generally been described as undesirable in the literature in amounts in excess of about 2% by weight. This is due to the alternative and generally favored reaction between carbon monoxide and hydrogen to reform methane which effectively lowers the yield of acetic acid. See for example European Patent Specification EP 0 526 974 B1 and U.S. Pat. No. 5,659,077. Accordingly, commercial processes using this route incorporate an intermediate separation step to remove the excess hydrogen from the feed prior to passing it into the carbonylation reactor. However, U.S. Pat. Nos. 5,189,203 and 5,286,900 suggest that this energy intensive gas separation step may be avoided by use of a rhodium catalyst and an methyl iodide promoter. In this instance, the hydrogen passes through the carbonylation step.

Products prepared from the Fischer-Tropsch process comprise a mixture of various liquid and solid hydrocarbons which are generally up-graded to higher value products such as lubricating base oils and transportation fuels. Upgrading processes for Fischer-Tropsch products include, but are not necessarily limited to, hydrogenation, hydrocracking, reforming, catalytic isomerization, hydrofinishing, and hydrotreating processes, all of which require hydrogen. One source of hydrogen which is commonly used in association with the Fischer-Tropsch process is by means of the water gas shift reaction (7) in which carbon monoxide recovered from the synthesis gas along with added water react to produce hydrogen gas and carbon dioxide.

$$CO + H_2O \rightarrow CO_2 + H_2 \quad (7)$$

In addition the tail gas from a Fischer-Tropsch plant usually contains large amounts of carbon dioxide as a result of the water gas shift reaction-taking place in the Fischer-Tropsch reactor. The carbon dioxide resulting from the water gas shift reaction to generate hydrogen and the tail gas from the Fischer-Tropsch reactor is usually recycled to the syngas reformer or, alternately, vented to the atmosphere as waste gas. Since carbon dioxide is one of the most significant green house gases, it is advantageous to find a way to either avoid generating carbon dioxide or use it to produce valuable products.

As used in this disclosure the words "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the composition. The phrases "consisting of" or "consists of" are intended as a transition meaning the exclusion of all but the recited elements with the exception of only minor traces of impurities.

SUMMARY OF THE INVENTION

The present invention is directed to an integrated process for manufacturing methanol, acetic acid, and Fischer-Tropsch products from synthesis gas without the need for a separate hydrogen generation step while reducing the production of carbon oxides as waste gas. Accordingly, the present invention may be described as an integrated process for making upgraded Fischer-Tropsch products and a carbonylation product which comprises one or more of acetic acid, methyl acetate, and acetic anhydride from synthesis gas comprising the steps of (a) separating the synthesis gas into a first portion and a second portion; (b) reacting the hydrogen and carbon monoxide from the first synthetic gas portion in a reaction zone in the presence of a catalyst under conditions preselected to form methanol; (c) recovering an intermediate product mixture comprising methanol, hydrogen and carbon monoxide from the reaction zone of step (b), wherein said intermediate reaction mixture contains at least 25% by volume of hydrogen; (d) contacting the intermediate product mixture recovered in step (c) in a carbonylation reaction zone under vapor phase conditions with a carbonylation catalyst containing one or more of a metal selected from the group consisting of rhodium, iridium, osmium, and cobalt on an inert support and a halide promoter under carbonylation conditions selected to produce a carbonylation product comprising one or more of acetic acid, methyl acetate, and acetic anhydride; (e) recovering separately hydrogen and the carbonylation product from the carbonylation reaction zone of step (d); (f) contacting the second synthetic gas portion of step (a) with a Fischer-Tropsch catalyst in a Fischer-Tropsch reaction zone under conditions preselected to produce Fischer-Tropsch products; (g) feeding the hydrogen recovered from step (e) into a hydroprocessing zone for upgrading Fischer-Tropsch products; (h) upgrading the Fischer-Tropsch products of step (f) in the hydroprocessing zone of step (g); and (i) recovering an upgraded Fischer-Tropsch product. The preferred source of the synthesis gas is by reforming methane or natural gas by means of one or more of reactions (1) or (2) or (3), above. However, one skilled in the art will recognize that other sources of synthesis gas may also be used to carry out the invention.

In another embodiment of the present invention, tail gas from a Fischer-Tropsch plant is employed to produce the methanol used to manufacture acetic acid in the carbonylation step. Tail gas from a Fischer-Tropsch plant typically will contain unreacted carbon monoxide and hydrogen as well as significant amounts of carbon dioxide which are formed by the water gas shift reaction which takes place as a side reaction in the Fischer-Tropsch reactor. Accordingly, the present invention is also directed to an integrated process for making upgraded Fischer-Tropsch products and a carbonylation product which comprises one or more of acetic acid, methyl acetate, and acetic anhydride from the tail gas from a Fischer-Tropsch plant which comprises a gaseous mixture of carbon oxides and hydrogen, said process comprising the steps of (a) recovering the tail gas from the Fischer-Tropsch plant and using it as feed to a methanol plant; (b) reacting the hydrogen and carbon oxides from the tail gas in a reaction zone of the methanol plant in the presence of a catalyst under conditions preselected to form methanol; (c) recovering an intermediate product mixture comprising methanol, hydrogen and carbon oxides from the reaction zone of step (b), wherein said intermediate reaction mixture contains at least 25% by volume of hydrogen; (d) contacting the intermediate product mixture recovered in step (c) in a carbonylation reaction zone under vapor phase conditions with a carbonylation catalyst containing one or more of a metal selected from the group consisting of rhodium, iridium, osmium, and cobalt on an inert support and a halide promoter under carbonylation conditions selected to produce a carbonylation product comprising one or more of acetic acid, methyl acetate, and acetic anhydride; (e) recovering separately hydrogen and the carbonylation product from the carbonylation reaction zone of step (d); (f) feeding the hydrogen recovered from step (e) into a hydroprocessing zone for upgrading Fischer-Tropsch products; (g) upgrading Fischer-Tropsch products from the Fischer-Tropsch plant in the hydroprocessing zone of step (f); and (h) recovering an upgraded Fischer-Tropsch product. As used in this disclosure the term "carbon oxides" refers to carbon dioxide and carbon monoxide. One skilled in the art will recognize that both carbon dioxide and carbon monoxide may be used in the production of methanol according to step (b) and as shown in reactions (4) and (5), however, only unconverted carbon monoxide participates in the carbonylation step, i.e. reaction (6) above.

The preferred carbonylation catalyst will contain rhodium or iridium as the active metal with rhodium being most preferred. The preferred halide promoter is methyl iodide or methyl bromide, with methyl iodide being especially preferred.

The carbonylation product recovered from the carbonylation is selected from any one of the group consisting essentially of acetic acid, methyl acetate, and acetic anhydride. In most cases the carbonylation product will comprise a mixture of two or more of these products, most especially a mixture of acetic acid and methyl acetate. Both methyl acetate and acetic anhydride are readily converted to acetic acid by processes recorded in the literature and familiar to those skilled in the art.

DETAILED DESCRIPTION OF THE INVENTION

Figure 1:
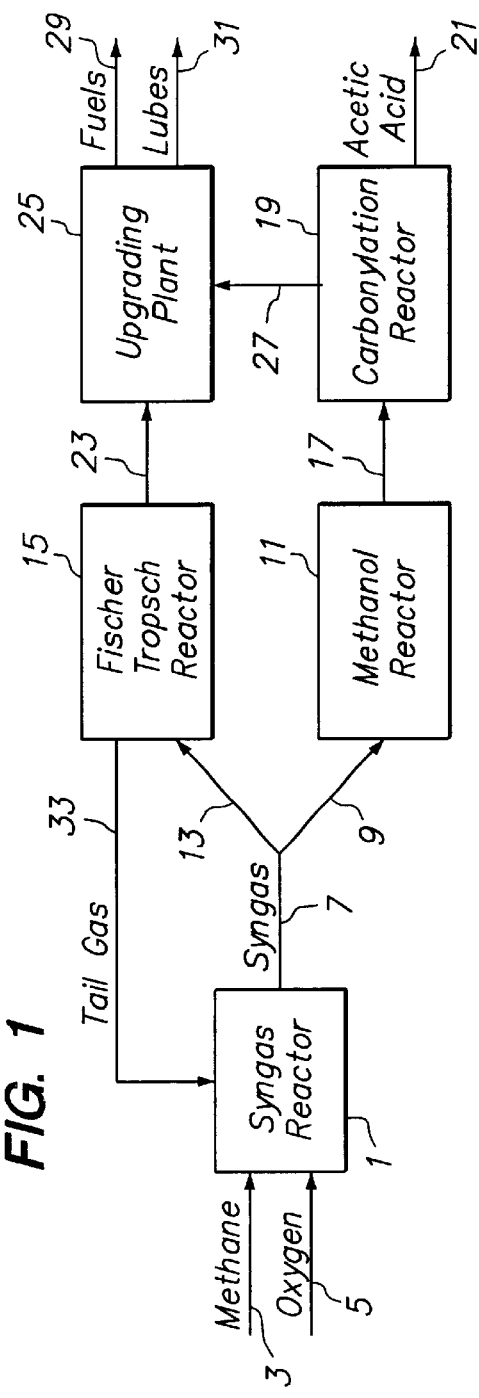
FIG. 1 illustrates, in block diagram, an embodiment of the invention in which a Fischer-Tropsch plant and an acetic acid plant are operated in parallel, wherein the synthesis gas is divided into two portions which are separately fed to each of the plants.

The present invention will be most readily understood by reference to the drawings. FIG. 1 illustrates, in block diagram, the parallel production of acetic acid and Fischer-Tropsch products and the synergies associated with the scheme. Methane, most likely in the form of natural gas, and oxygen are fed into a syngas reactor 1 via feed inlets 3 and 5, respectively. The synthesis gas generated in the syngas reactor exits via conduit 7 and is split into two feed streams. One syngas feed stream 9 goes to a methanol reactor 11. The second syngas feed stream is routed to the Fischer-Tropsch reactor 15 by line 13. In the methanol reactor 11, the carbon monoxide and hydrogen in the synthesis gas are reacted over a catalyst, typically a copper-based catalyst, to form methanol. As noted above any carbon dioxide which may be present in the syngas also will react with the hydrogen to form methanol. Conduit 17 carries a mixture of methanol along with unreacted carbon monoxide and hydrogen to the carbonylation reactor 19. In the carbonylation reactor, methanol and carbon monoxide are reacted over a rhodium catalyst promoted with methyl iodide to produce acetic acid, the corresponding ester methyl acetate, or acetic anhydride. The methyl acetate and acetic anhydride are readily converted to acetic acid by a hydrolysis reaction (not shown in the figure) and the acetic acid is recovered via product line 21. The overhead gases from the carbonylation reactor comprising mostly hydrogen, but also containing various amounts of methane, carbon dioxide and carbon monoxide, is recovered by line 27. The syngas routed via line 13 to the Fischer-Tropsch reactor 15 is contacted in the reactor with a Fischer-Tropsch catalyst where the carbon monoxide and hydrogen react to form Fischer-Tropsch crude products which generally comprise a mixture of $C_1$ to $C_{200}$ plus hydrocarbons, most falling within the $C_5$ to $C_{100}$ plus range. The majority of the crude Fischer-Tropsch products require upgrading before they will constitute a suitable commercial product, i.e., jet fuel, diesel fuel, lube base stock, fully refined wax, gasoline and the like. The crude Fischer-Tropsch products are recovered in line 23 and sent to an upgrading plant 25 which in most instances will constitute more than a single hydroprocessing unit but for the sake of simplicity is shown as a single unit. In the upgrading plant the crude Fischer-Tropsch products will be mixed with hydrogen from line 27 over an appropriate hydroprocessing catalyst and under the appropriate hydroprocessing conditions to produce the desired higher value products, which in the figure are shown as being recovered via lines 29 and 31 as fuel and lube base oils, respectively. Carbon oxides which are present as contaminating gases along with the hydrogen in line 27 will act as poisons to some upgrading catalysts, such as those used in hydrocracking, and must be removed or converted prior to sending the hydrogen and accompanying gases to the upgrading plant. In most cases the carbon oxides will be converted to methane before being passed to the upgrading plant. Tail gas from the Fischer-Tropsch reactor 15 is recycled by means of line 33 to the syngas reactor. Thus the carbon dioxide in the tail gas need not be vented into the atmosphere but is routed from the syngas reactor via lines 7 and 9 to the methanol reactor where it is converted into methanol through reaction (5) above. Any methane present in the tail gas will be converted to additional syngas in the syngas reactor. Likewise, there is no need for an expensive hydrogen separation step between the methanol reactor 11 and the carbonylation reactor 19. In addition, the overhead gases from the upgrading plant may be recycled back to the syngas unit for further processing (not shown). Thus operation according to the present invention is very efficient with most of the feed being converted to product and with minimal greenhouse gas being released.

Figure 2:
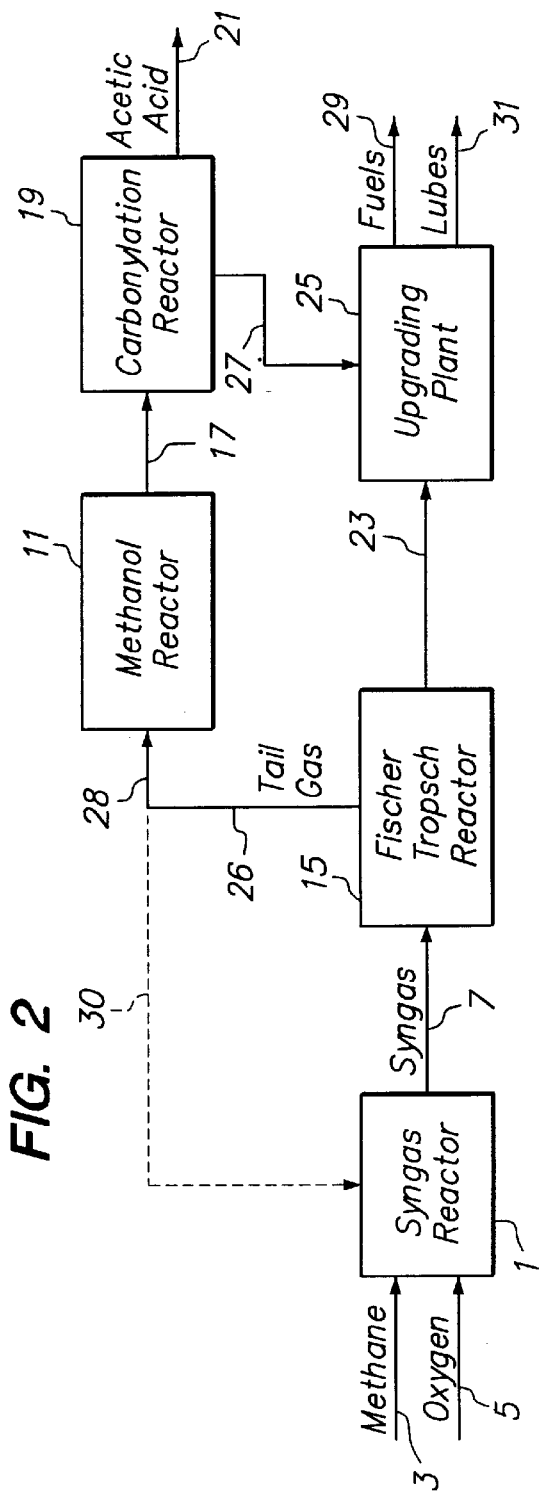
FIG. 2 illustrates, in block diagram, a process scheme in which the Fischer-Tropsch plant and the acetic acid plant are operated in sequence, wherein the tail gas from the Fischer-Tropsch plant serves as feed stock to the acetic acid plant.

FIG. 2 illustrates an alternative embodiment of the invention in which the Fischer-Tropsch unit and the acetic acid unit are arranged sequentially using the tail gas from the Fischer-Tropsch reactor as the feed for methanol production. In this embodiment the methane 3 and the oxygen 5 are fed into the syngas reactor 1. The syngas 7 is fed into the Fischer-Tropsch reactor where the crude Fischer-Tropsch products are produced which in turn are routed via line 23 to the upgrading plant 25. The tail gas from the Fischer-Tropsch reactor 15 is collected in line 26 and routed to the methanol reactor 11 via line 28. Optionally, a portion of the tail gas may be recycled to the syngas reactor by means of line 30. In the methanol reactor, a portion of the tail gas, which comprises mostly carbon dioxide, carbon monoxide, and hydrogen, is converted to methanol by means of reactions (4) and (5). The output from the methanol reactor comprising a mixture of methanol, carbon monoxide, and hydrogen passes to the carbonylation unit 19 via conduit 17. The acetic acid is recovered from the carbonylation unit by product line 21 and the overhead gases comprising primarily hydrogen with some methane and carbon oxides present is routed to the upgrading plant by means of line 27. As previously noted, carbon oxides mixed with the hydrogen will usually be converted to methane prior to being sent to the upgrading plant. Following upgrading the fuels and lube base oils are recovered via lines 29 and 31, respectively. Overhead gases from the upgrading plant, which will comprise primarily hydrogen, carbon dioxide, and methane, may be recycled (not shown) to the syngas reactor.

Feedstocks

Natural gas which may be used to generate the synthesis gas used as a feed stock in the present invention is an abundant fossil fuel resource. Recent estimates place worldwide natural gas reserves at about $35 \times 10^{14}$ standard cubic feet, corresponding to the energy equivalent of about 637 billion barrels of oil. The composition of natural gas at the wellhead varies, but the major hydrocarbon present is methane. For example the methane content of natural gas may vary within the range of from about 40 vol. % to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3$ plus hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Since much of the known reserves for natural gas are found along with crude oil in locations where it not economical to ship the gas to market, the natural gas under such circumstances is often flared or re-injected into the well. In either case the economic value of the natural gas is lost. The present invention makes it possible to convert the methane in the natural gas into higher value products, i.e., transportation fuel, lubricating base oil, methanol, and acetic acid. In addition, since almost all of the carbon value in the natural gas is converted into products, minimal carbon dioxide is released into the atmosphere.

It is also possible to use methane derived from other sources in the process of the present invention. Methane can be derived from a variety of sources, such as the fuel gas system; the gasification of the heavy carbonaceous materials such as may be found in coal, coker bottoms, and residuum; or even the reduction of methanol. For example, a process for making syngas from coal suitable for use in the production of methanol is disclosed in U.S. Pat. 4,971,683 which is incorporated herein in its entirety. This patent discloses that coal can be processed to produce hydrocarbon-containing liquids and methanol by first using short residence time reactions to produce petroleum substitutes and chemical feedstocks at lower pressures and higher volatilization temperatures to effect higher heating rates without attendant gas production and/or "condensation" reactions, thereby producing high hydrocarbon liquid yields and then partially oxidizing the solid char produced to yield sour syngas which consists primarily of CO and $H_2$ with lesser amounts of $CO_2$, $H_2S$, $CH_4$, $NH_3$ and $N_2$. In accordance with another embodiment, the synthesis gas from char gasification is reacted with water in a so-called "shift reactor" to produce a $H_2$ to CO ratio in excess of that required to produce methanol, i.e., $H_2$ to CO ratio greater than 2.1. The gas exiting the shift reactor is then sweetened to remove acid gas ($H_2$ S and $CO_2$). The sweetened gas is then sent to a conventional methanol synthesis unit and Fischer-Tropsch unit where methanol and Fischer-Tropsch products, respectively, are produced.

Synthesis Gas

Typically, synthesis gas contains hydrogen and carbon monoxide, and may include minor amounts of carbon dioxide and/or water. The presence of certain contaminants, such as sulfur, nitrogen, halogen, selenium, phosphorus and arsenic contaminants in the syngas are undesirable. For this reason, it is preferred to remove sulfur and other contaminants from the feed before performing the Fischer-Tropsch chemistry. Means for removing these contaminants are well known to those of skill in the art. For example, ZnO guardbeds are preferred for removing sulfur impurities. Means for removing other contaminants are well known to those of skill in the art.

The synthesis gas used to carry out the present invention can be generated using steam methane reforming, partial oxidation or gasification, or a combined reforming or autothermal reforming process.

Steam methane reforming is the catalytic reaction of natural gas with steam to produce a synthesis gas or "syngas", which includes $H_2$, $CO_2$, CO, $CH_4$, and $H_2O$ with an $H_2$ to CO ratio of about 3:1 or higher. The steam methane reformation reaction is endothermic. Therefore, external heat is required. The natural gas and steam are typically fed into alloy tubes that contain a nickel-based catalyst for the reforming reaction. The catalyst tubes are placed inside a refractory lined structure. A portion of the natural gas is used as fuel to provide the heat required for the reaction:

$$H_2O + CH_4 \rightarrow 3H_2 + CO \qquad (2)$$

The drawbacks of steam methane reforming include its limitation to low pressure applications on the order of about 100 psig to about 400 psig. Steam methane reforming also produces a syngas with a high $CH_4$ impurity content in a range of about 3% to about 15%, and requires the external supply of $CO_2$ for methanol syngas requirements. As discussed below, low temperature methanol processes have recently become available which will operate at lower pressures than conventional processes. Accordingly, these processes make the use of steam reforming more practical for synthesis gas generation when used in the present invention.

Partial oxidation or gasification is a non-catalytic reaction of natural gas with oxygen under controlled oxygen conditions. The reaction is exothermic as shown in the following reaction:

$$2CH_4 + O_2 \rightarrow 2CO + 4H_2 \qquad (1)$$

The partial oxidation process can be operated at high pressure to minimize or eliminate the syngas compression needed to reach the desired elevated pressure suitable for methanol production, typically about 200 psig to about 2000 psig. However, the syngas produced from the partial oxidation process has a lower $H_2$:CO ratio with little or no $CH_4$ content. Typically, the $CH_4$ varies from about 0% to about 0.5%, and the $H_2$:CO ratio varies from about 1.5 to about 2.0. As a result, external $H_2$ is often needed to meet the methanol syngas requirements.

The combined reforming process uses a combination of conventional steam methane reforming, often referred to as "primary reforming", in combination with oxygenated catalytic reforming, often referred to as "secondary reforming", to generate stoichiometric ratioed synthesis gas for the production of methanol. See U.S. Pat. No. 4,888,130. In a preferred aspect of the combined reforming process, a portion of the natural gas feedstock is fed to the primary reformer and the effluent is blended with the balance of the natural gas and oxygen prior to entering the secondary reformer. The drawback of the combined reforming process is that it is limited to moderate pressure applications, on the order of about 400 psig to about 600 psig. At higher pressures, reduced operating temperatures are necessary, and because increased amounts of $CH_4$ are present in the feed to the secondary reformer, it is more likely that soot or carbon formation will be increased. This can damage or deactivate the catalyst and lead to greater feed consumption to produce the required amount of carbon monoxide. As already noted, the newer low temperature methanol processes are able to operate at lower pressures which makes combined reforming a more viable option economically for syngas generation.

Methanol Production

Most commercial methanol production currently being carried out uses various copper-based catalyst systems. A practical operating pressure for the methanol synthesis plant when using a copper based catalyst is in the range of about 700 psig to about 2000 psig depending on the technology used. A number of different state-of-the-art technologies are known for synthesizing methanol, and are commonly referred to as the ICI (Imperial Chemical Industries) process, the Lurgi process, the Air Products "LP Methanol process", and the Mitsubishi process.

The methanol syngas, also referred to as "stoichiometric ratioed synthesis gas", from the syngas generation unit is fed to a methanol synthesis reactor at the desired pressure which will depend upon the process employed. The syngas then reacts over a copper-based catalyst to form methanol. The reaction using convention copper-based catalysts is exothermic. Therefore, heat removal is required. In the event that part of the methanol production is not used to manufacture acetic acid, but is recovered for sale, the raw or impure methanol may be condensed and purified to remove impurities, such as water and higher alcohols including ethanol, propanol, and the like. The uncondensed vapor phase comprising unreacted methanol syngas may be recycled to the feed.

For optimal methanol production, the stoichiometric ratioed syngas supplied to the methanol synthesis unit generally conforms to the following specifications:

$$H_2 - CO_2$$

$$CO + CO_2 = 1.9 - 2.1$$

and $N_2$, Ar, and $CH_4 \leq 3.0\%$

For the purposes of manufacturing a carbonylation product according to the present invention, it is unnecessary to further purify the crude methanol. In this instance, the products of the methanol reaction, including the crude methanol, unreacted carbon oxides and hydrogen are feed into the carbonylation reactor.

The production of methanol using conventional copper catalysts requires that the synthesis gas be compressed to a relatively high pressure, which necessitates the use of compressors and increases the cost of carrying out the methanol step of the present process. Therefore, it is advantageous in carrying out the present invention to utilize one of the newer more active catalysts, such as nickel carbonyl or palladium on cerium oxide, in carrying out the methanol synthesis. These processes referred to as low temperature methanol processes allow the production of methanol to be carried out at a lower temperature and under lower pressure resulting in significant cost savings.

Carbonylation

As discussed above, the present invention includes a carbonylation reaction for the formation of a carbonylation product, the most preferred product of which is acetic acid:

$$CO + CH_3OH \rightarrow CH_3COOH \quad (6)$$

However, other preferred carbonylation products may include methyl acetate and acetic anhydride or mixtures of any two or all three products depending on the exact conditions and reactants present in the carbonylation reaction section. Methyl acetate can and typically does form in the carbonylation reaction section as follows:

$$CH_3COOH + CH_3OH \rightarrow CH_3COOCH_3 + H_2O \quad (8)$$

or:

$$CH_3OCH_3 + CO \rightarrow CH_3COOCH_3 \quad (9)$$

Acetic anhydride can form in the carbonylation reaction section (particularly in the absence of water) by the following reactions:

$$CH_3OCH_3 + 2CO \rightarrow (CH_3CO)_2O \quad (10)$$

$$CH_3COOCH_3 + CO \rightarrow (CH_3CO)_2O \quad (11)$$

Hydrolysis of the methyl acetate and acetic anhydride can occur if water is present in the carbonylation section according to the following reactions:

$$CH_3COOCH_3 + H_2O \rightarrow CH_3COOH + CH_3OH \quad (12)$$

$$(CH_3CO)_2O + H_2O \rightarrow 2CH_3COOH \quad (13)$$

$$(CH_3CO)_2 + CH_3OH \rightarrow CH_3COOH + CH_3COOCH_3 \quad (14)$$

The presence of water tends to facilitate the formation of acetic acid.

The carbonylation reaction takes place in the vapor phase over a halide promoted catalyst which comprises a metal selected from the group consisting of rhodium, iridium, osmium, and cobalt on an inert support. The preferred active metal for use in the catalyst is rhodium with iridium also representing a preferred embodiment. As used in this disclosure the term "inert support" refers to a support having essentially no catalytic activity of its own under the conditions in the carbonylation reaction zone. Examples of an inert support include conventional inert support materials such as alumina, silica, molecular sieves, or carbon supports. Typical examples of an inert carbon support used in a carbon-supported rhodium metal catalyst suitable for use in the carbonylation step may include inorganic supports such as carbon-supporting silica, alumina, zeolite, and the like, in addition to activated carbon, carbon black, coke, etc. Of these, activated carbon is preferred.

The amount of rhodium metal present on a carbon-supported rhodium metal catalyst that is preferred for practicing the invention is not specifically limited, but usually will fall within the range of from about 0.01% to about 20% by weight, preferably about 0.1% to about 10% by weight, and more preferably about 1% to about 5% by weight based on the total weight of the catalyst.

The rhodium metal may be deposited from a rhodium reagent on the inert support by processes well known to those skilled in the art and may include impregnation, deposition, immersion, metallizing, kneading, and the like.

Examples of rhodium reagents which may be used may include rhodium chloride, sodium chlororhodate, ammonium chlororhodate, rhodium hydroxide and the like. Of these, rhodium chloride is particularly preferred.

Following deposition of the metal the catalyst water is evaporated by drying, usually within a temperature range of between 50° C. to 200° C., preferably between 80° C. to 120° C. After drying, the catalyst is usually reduced under a hydrogen atmosphere by flowing a hydrogen-containing gas through the catalyst at between 100° C. and 700° C., preferably between 200° C. to 400° C. Reduction of the catalyst may alternatively be carried out in the liquid phase by use of a combination of formalin with alkali. The reduction may also be carried out in the carbonylation reactor, in which case a separate reduction step may be unnecessary.

The halide promoter is preferably a methyl halide, most preferably either methyl iodide or methyl bromide. Methyl iodide is most preferred as the promoter. The amount of methyl halide used to promote the carbonylation reaction is not specifically limited, but is usually within the range of from about 0.1 mole to about 50 moles, preferably within the range of 1 mole to 20 moles per 100 moles of methanol. Examples of iodine compounds that may be useful carrying out the carbonylation step in place of methyl iodide include, but are not limited to, iodine, hydrogen iodide, and other iodine compounds which are capable of forming methyl iodide by reaction with methanol in the carbonylation reactor. Bromide compounds may also be used in the process of the present invention. Examples of bromide compounds that may be added to the carbonylation reactor, include but are not limited to, bromine, and hydrogen bromide, as well as other bromides which are capable of forming methyl bromide by reaction with methanol in the reaction system.

The presence of water in the carbonylation reactor may be desirable because its presence increases the selectivity for acetic acid and decreases the selectivity for the less desirable methyl acetate, resulting in an increase in the yield of acetic acid. Preferably, the amount of water present in the carbonylation reactor is in the range of from about 3 mol % to about 50 mol % relative to the amount of methanol present. When the water falls below about 3 mol % the amount of methyl acetate formed in the carbonylation step usually will be higher than desired. However, when the amount of water exceeds about 50 mol % the partial pressures of carbon monoxide and methanol become reduced to a point where the level of conversion of methanol to acetic acid becomes unsatisfactory.

The carbonylation step is usually carried out by contacting the intermediate product mixture recovered from the methanol reactor with the rhodium metal catalyst and methyl iodide promoter in vapor phase under conditions selected to favor the formation of the desired carbonylation product. In general, these conditions will include a methanol to carbon monoxide molar ratio of between about 1:100 to about 100:1, preferably about 1:10 to about 10:1; a reaction temperature of from about 100° C. to about 400° C., preferably from about 150° C. to about 220° C., more preferably from about 180° C. to about 200° C. At temperatures in excess of 220° C. the production of methane increases reducing the yield of the desired carbonylation product. In addition, maintaining the reactants in the carbonylation reactor in the vapor phase is essential to the present invention in order to reduce the amount of corrosion of the process equipment. Accordingly, a combination of temperature and pressure is selected to maximize the conversion while maintaining the mixture above its dew point in order to prevent the leaching of metal from the catalyst or cause liquid phase corrosion.

The reactor used in the carbonylation step may be of the fixed catalyst bed type, fluidized bed type or moving bed type. The preferred reactor design for carrying out this step is of the fixed bed type.

Purification of the acetic acid product has been described in the literature and is practiced commercially. Therefore, a detailed discussion should not be necessary here in order for one skilled in the art to prepare commercial grade acetic acid. In general, low boiling substances such as dimethyl ether and methyl acetate may be removed from the chilled acetic acid reactor effluent by distilling up to a cut point of about 175° F. (80° C.). Any rhodium catalyst remaining in the bottoms may be recovered by flash-distillation. The flash distilled acetic acid is azeotropically dehydrated. A final distillation may be used to obtain glacial acetic acid. Any iodine remaining in the product may be removed by fractional distillation.

Fischer-Tropsch Process

In the Fischer-Tropsch synthesis process solid, liquid and gaseous hydrocarbons are formed by contacting the synthesis gas with a Fischer-Tropsch catalyst under suitable temperature and pressure. The Fischer-Tropsch reaction is typically conducted at temperatures of about from 300° F. to 700° F. (149° C. to 371° C.) preferably about from 400° F. to 550° F. (204° C. to 228° C.); pressures of from about 10 psia to about 600 psia, (0.7 bar to 41 bars) preferably 30 psia to 300 psia, (2 bars to 21 bars) and catalyst space velocities of about from 100 cc/g/hr. to 10,000 cc/g/hr., preferably 300 cc/g/hr. to 3,000 cc/g/hr.

The crude Fischer-Tropsch products, i.e. the Fischer-Tropsch products recovered from the Fischer-Tropsch reactor prior to upgrading, may range from $C_1$ to $C_{200}$ plus hydrocarbons, with a majority in the $C_5$–$C_{100}$ plus range. The reaction can be conducted in a variety of reactor types, for example, fixed bed reactors containing one or more catalyst beds, slurry reactors, fluidized bed reactors, or a combination of different type reactors. Such reaction processes and reactors are well known and documented in the literature. Slurry Fischer-Tropsch processes, which is a preferred embodiment in the practice of the invention, utilizes superior heat (and mass) transfer characteristics for the strongly exothermic synthesis reaction and are able to produce relatively high molecular weight, paraffinic hydrocarbons when using a cobalt catalyst. In a slurry process, the syngas is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. A particularly preferred embodiment of the Fischer-Tropsch process is taught in EP0609079, which is incorporated herein by reference for all purposes.

Suitable Fischer-Tropsch catalysts comprise one or more Group VIII catalytic metals, such as Fe, Ni, Co, Ru and Re. Additionally, a suitable catalyst may contain a promoter. Thus, a preferred Fischer-Tropsch catalyst comprises effective amounts of cobalt and one or more of Re, Ru, Pt, Fe, Ni, Th, Zr, Hf, U, Mg, and La on a suitable inorganic support material, preferably one which comprises one or more refractory metal oxides. In general, the amount of cobalt present in the catalyst is between about 1 weight % and about 50 weight % of the total catalyst composition. The catalysts can also contain basic oxide promoters such as $ThO_2$, $La_2O_3$, $MgO$, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Support materials including alumina, silica, magnesia and titania or mixtures thereof may be used. Preferred supports for cobalt containing catalysts comprise titania. Useful catalysts and their preparation are known and illustrative, but non-limiting examples may be found, for example, in U.S. Pat. No. 4,568,663.

The products from the Fischer-Tropsch reactor generally will include a gaseous product comprising primarily $C_4$ minus hydrocarbons, a liquid product comprising about $C_5$ to about $C_{20}$ hydrocarbons, and a solid wax comprising mostly $C_{20}$ plus hydrocarbons. The gaseous fraction will also include tail gases such as methane and carbon oxides. The tail gas and light hydrocarbons may be routed either directly to the methanol reactor or to the syngas reactor. The methane and other light hydrocarbons will be converted into synthesis gas in the syngas reactor, and the carbon oxide will react with hydrogen in the methanol plant to form methanol. Each gas may be recycled through the integrated process constituting the present invention which results in the efficient conversion of what would otherwise be waste gas into valuable products and in the reduction of greenhouse gas emissions into the atmosphere.

The liquid and wax fractions recovered from the Fischer-Tropsch plant will be upgraded in a upgrading plant which will include various hydroprocessing operations. The particular hydroprocessing operation will depend on the desired products. The term hydroprocessing, as used in this disclosure, is intended to mean a process requiring free hydrogen which is intended to upgrade Fischer-Tropsch products into higher value products. As used herein, hydroprocessing may include, but is not necessarily limited to, hydrogenation, hydrotreating, hydrofinishing, hydrocracking, isomerization, denitrification, and reforming.

In some embodiments, the product stream from the Fischer-Tropsch plant may contain a relatively large amount of olefins that may be hydrogenated. Optionally, these olefins can be isomerized or oligomerized prior to hydrogenation to provide branched paraffins. Branching may be advantageous in a number of end-uses, particularly when increased octane values or decreased pour points are desired.

After the reaction mixture is converted to the final product stream, the desired products can be isolated, for example, by distillation. $C_5$–$C_{12}$ products can be isolated and used, for example, as transportation fuels. Higher molecular weight products can either be isolated and used directly, or can be further processed to form lower molecular weight products. For example, high molecular weight products can be hydrocracked to provide lower molecular weight products, increasing the yield of liquid transportation fuels.

The following examples of hydroprocessing operations is intended to be illustrative only and is not intended to be a limitation on the scope of the invention. Hydrocracking refers to a catalytic process, usually carried out in the presence of free hydrogen in which the cracking of the larger hydrocarbon molecules is the primary purpose of the operation. Hydrotreating is a less severe hydroprocessing operation in which the amount of cracking is minimized. Hydrotreating may be used to remove oxygenates and nitrogen-containing contaminants from the products. Hydrofinishing is intended primarily to saturate the double bonds in order to improve the stability, usually defined as the UV stability, of the product. Reforming is a hydroprocessing operation in which normally liquid hydrocarbons, particularly hydrocarbons intended for transportation fuels, are contacted with a catalyst in the presence of free hydrogen in order to increase the aromatic content of the fuel. In the present invention at least part, preferably all, of the hydrogen used in the various hydroprocessing operations will be that recovered from the acetic acid plant.

Like the tail gases recovered from the Fischer-Tropsch plant, the overhead gases from the various hydroprocessing operations will typically contain significant quantities of hydrogen, $C_4$ minus hydrocarbons, methane, and carbon dioxide. These gases may be routed back either to the syngas reactor or mixed with the syngas entering the methanol reactor. The most advantageous use of the overhead gases will depend on their composition. For example, if they contain large amounts of methane, it would generally be desirable to route them through the syngas reactor.

What is claimed is:

1. An integrated process for making upgraded Fischer-Tropsch products and a carbonylation product comprising one or more of acetic acid, methyl acetate, and acetic anhydride from synthesis gas comprising the steps of:

(a) separating the synthesis gas into a first portion and a second portion;

(b) reacting the hydrogen and carbon monoxide from the first synthetic gas portion in a reaction zone in the presence of a catalyst under conditions preselected to form methanol;

(c) recovering an intermediate product mixture comprising methanol, hydrogen and carbon monoxide from the reaction zone of step (b), wherein said intermediate reaction mixture contains at least 25% by volume of hydrogen;

(d) contacting the intermediate product mixture recovered in step (c) in a carbonylation reaction zone under vapor phase conditions with a carbonylation catalyst containing one or more of a active metal selected from the group consisting of rhodium, iridium, osmium, and cobalt on an inert support and a halide promoter under carbonylation conditions to produce a carbonylation product is formed comprising one or more of acetic acid, methyl acetate, and acetic anhydride;

(e) recovering separately hydrogen and the carbonylation product from the carbonylation reaction zone of step (d);

(f) contacting the second synthetic gas portion of step (a) with a Fischer-Tropsch catalyst in a Fischer-Tropsch reaction zone under conditions preselected to produce Fischer-Tropsch products;

(g) feeding the hydrogen recovered from step (e) into a hydroprocessing zone for upgrading Fischer-Tropsch products;

(h) upgrading the Fischer-Tropsch products of step (f) in the hydroprocessing zone of step (g); and (i) recovering an upgraded Fischer-Tropsch product.

2. The process of claim 1 wherein the synthesis gas is supplied by reforming methane.

3. The process of claim 2 wherein the synthesis gas is supplied by steam reforming of methane.

4. The process of claim 2 wherein the synthesis gas is supplied by reforming the methane with oxygen.

5. The process of claim 1 wherein the synthesis gas is supplied by the gasification of heavy carbonaceous materials.

6. The process of claim 5 wherein the heavy carbonaceous is coal.

7. The process of claim 1 wherein the methanol formed in step (b) is produced by a low temperature methanol process.

8. The process of claim 7 wherein the catalyst used in the low temperature methanol process is nickel carbonyl.

9. The process of claim 7 wherein the catalyst used in the low temperature methanol process is palladium on cerium oxide.

10. The process of claim 1 wherein the intermediate product mixture of step (c) contains at least 35% by volume of hydrogen.

11. The process of claim 10 wherein the intermediate product mixture of step (c) contains at least 45% by volume of hydrogen.

12. The process of claim 1 wherein the metal rhodium is present in the carbonylation catalyst.

13. The process of claim 1 wherein the metal iridium is present in the carbonylation catalyst.

14. The process of claim 1 wherein the halide promoter present in the carbonylation zone is selected methyl iodide or methyl bromide.

15. The process of claim 14 wherein the halide promoter is methyl iodide.

16. The process of claim 1 wherein tail gas generated in the Fischer-Tropsch reaction zone is recovered and mixed with the synthesis gas from step (a).

17. The process of claim 1 wherein tail gas generated in the Fischer-Tropsch reaction zone is recovered and mixed with the first synthetic gas portion of step (b).

18. The process of claim 1 wherein overhead gases from the hydroprocessing zone are recovered and mixed with the synthesis gas from step (a).

19. The process of claim 1 wherein overhead gases from the hydroprocessing zone are recovered and mixed with the first synthetic gas portion of step (b).

20. An integrated process for making upgraded Fischer-Tropsch products and a carbonylation product which comprises acetic acid, methyl acetate, and acetic anhydride from the tail gas from a Fischer-Tropsch plant which comprises a gaseous mixture of carbon oxides and hydrogen, said process comprising the steps of:

(a) recovering the tail gas from the Fischer-Tropsch plant and using it as feed to a methanol plant;

(b) reacting the hydrogen and carbon oxides from the tail gas in a reaction zone of the methanol plant in the presence of a catalyst under conditions preselected to form methanol;

(c) recovering an intermediate product mixture comprising methanol, hydrogen and carbon oxides from the reaction zone of step (b), wherein said intermediate reaction mixture contains at least 25% by volume of hydrogen;

(d) contacting the intermediate product mixture recovered in step (c) in a carbonylation reaction zone under vapor phase conditions with a carbonylation catalyst containing one or more of a metal selected from the group consisting of rhodium, iridium, osmium, and cobalt on an inert support and a halide promoter under carbonylation conditions selected to produce a carbonylation product comprising of one or more of acetic acid, methyl acetate, and acetic anhydride;

(e) recovering separately hydrogen and the carbonylation product from the carbonylation reaction zone of step (d);

(f) feeding the hydrogen recovered from step (e) into a hydroprocessing zone for upgrading Fischer-Tropsch products;

(g) upgrading Fischer-Tropsch products from the Fischer-Tropsch plant in the hydroprocessing zone of step (f); and (h) recovering an upgraded Fischer-Tropsch product.

21. The process of claim 20 wherein the methanol formed in step (b) is produced by a low temperature methanol process.

22. The process of claim 21 wherein the catalyst used in the low temperature methanol process is nickel carbonyl.

23. The process of claim 21 wherein the catalyst used in the low temperature methanol process is palladium on cerium oxide.

24. The process of claim 20 wherein the intermediate product mixture of step (c) contains at least 35% by volume of hydrogen.

25. The process of claim 24 wherein the intermediate product mixture of step (c) contains at least 45% by volume of hydrogen.

26. The process of claim 20 wherein overhead gases from the hydroprocessing zone are recovered and mixed with the tail gas from the Fischer-Tropsch plant.

27. The process of claim 20 wherein synthesis gas supplied as feed to the Fischer-Tropsch plant is made by reforming methane.

28. The process of claim 27 wherein the tail gases from the Fischer-Tropsch plant is recycled by mixing it with the synthesis gas.

29. The process of claim 20 wherein the synthesis gas supplied as feed to the Fischer-Tropsch plant is made by the gasification of a heavy carbonaceous material.

30. The process of claim 29 wherein the heavy carbonaceous material is coal.

31. The process of claim 20 wherein the metal rhodium is present in the carbonylation catalyst.

32. The process of claim 20 wherein the metal iridium is present in the carbonylation catalyst.

33. The process of claim 20 wherein the halide promoter present in the carbonylation zone is methyl iodide or methyl bromide.

34. The process of claim 33 wherein the halide promoter is methyl iodide.

* * * * *